United States Patent
Akiyama et al.

(10) Patent No.: US 12,278,001 B2
(45) Date of Patent: Apr. 15, 2025

(54) INFORMATION PROCESSING DEVICE, INFORMATION PROCESSING METHOD, RECORDING MEDIUM RECORDING INFORMATION PROCESSING PROGRAM, AND INFORMATION PROCESSING SYSTEM

(71) Applicant: Ahead Biocomputing, Co. Ltd., Kawasaki (JP)

(72) Inventors: Yutaka Akiyama, Tokyo (JP); Masahito Ohue, Tokyo (JP); Keisuke Yanagisawa, Tokyo (JP); Yasushi Yoshikawa, Tokyo (JP)

(73) Assignee: Ahead Biocomputing, Co. Ltd., Kawasaki (JP)

( * ) Notice: Subject to any disclaimer, the term of this patent is extended or adjusted under 35 U.S.C. 154(b) by 505 days.

(21) Appl. No.: 17/524,758

(22) Filed: Nov. 12, 2021

(65) Prior Publication Data
US 2022/0157407 A1  May 19, 2022

(30) Foreign Application Priority Data
Nov. 13, 2020 (JP) .................... 2020-189856
Feb. 17, 2021 (JP) .................... 2021-023750

(51) Int. Cl.
G16C 20/30 (2019.01)
G16C 20/10 (2019.01)
G16C 20/70 (2019.01)

(52) U.S. Cl.
CPC ............ *G16C 20/30* (2019.02); *G16C 20/10* (2019.02); *G16C 20/70* (2019.02)

(58) Field of Classification Search
None
See application file for complete search history.

(56) References Cited

U.S. PATENT DOCUMENTS

| 6,801,861 | B2 * | 10/2004 | Mayo | C12N 15/1034 |
| | | | | 506/14 |
| 2010/0121791 | A1 * | 5/2010 | Kang | G16B 15/30 |
| | | | | 703/2 |
| 2011/0076275 | A1 | 3/2011 | Igawa et al. | |
| 2015/0030968 | A1 | 10/2015 | Bae et al. | |
| 2015/0300968 | A1 | 10/2015 | Bae et al. | |
| 2016/0253469 | A1 * | 9/2016 | Donovan | G16Z 99/00 |
| | | | | 705/2 |

(Continued)

FOREIGN PATENT DOCUMENTS

| CA | 2398892 A1 * | 8/2001 | ............ G16C 20/30 |
| CA | 3065653 | 1/2020 | |
| JP | 2017-037378 | 2/2017 | |

(Continued)

OTHER PUBLICATIONS

Akiyama et al. "Middle Molecule IT-Based Drug Discovery Laboratory (MIDL)", Presentation Materials for the Kanagawa Shonan Health Innovation Park Seminar, p. 1-40, Nov. 15, 2019.

(Continued)

*Primary Examiner* — Raul J Rios Russo
*Assistant Examiner* — Carl F. R. Tchatchouang

(57) ABSTRACT

In response to request signals transmitted from a terminal, a server generates prediction information relating to pharmacokinetics of a peptide. The server then transmits the prediction information to the terminal.

14 Claims, 15 Drawing Sheets

(56) References Cited

U.S. PATENT DOCUMENTS

2017/0357752 A1* 12/2017 Diggans .................. G05B 15/00
2021/0327553 A1* 10/2021 Lee ......................... G06N 20/00

FOREIGN PATENT DOCUMENTS

| JP | 2019-028879 | 2/2019 | |
|---|---|---|---|
| JP | 2019-179356 | 10/2019 | |
| JP | 2020-519246 | 7/2020 | |
| JP | 2020-523010 | 8/2020 | |
| KR | 100924328 | 11/2009 | |
| WO | WO 03/054743 | 7/2003 | |
| WO | WO-2020237139 A1 * | 11/2020 | ............. G16H 50/20 |

OTHER PUBLICATIONS

Akiyama et al. "Prediction of Membrane Permeability and Plasma Protein Binding of Cyclic Peptides", Presentation Materials for the AHeDD2019/IPAB2019 Joint Symposium, Tokyo, Japan, p. 1-25, Nov. 27-29, 2019.

Japan Intellectual Property Society "[Email to Inquire About the Release Date of the Proceedings of the 17th Annual Conference of the Japan Intellectual Property Society]", Proceedings of the 17th Annual Conference of the Japan Intellectual Property Society, p. 1-4, Dec. 2, 2019.

Japan Intellectual Property Society "[Information Technology and Intellectual Property]", Presentation Materials of the 17th Annual Conference of the Japan Intellectual Property Society, Tokyo, Japan, Dec. 7-8, 2019, p. 1-10, Dec. 2, 2019.

Japan Intellectual Property Society "[Program of the 17th Annual Conference of the Japan Intellectual Property Society]", 17th Annual Conference of the Japan Intellectual Property Society, Tokyo, Japan, p. 1-3, Dec. 7-8, 2019.

Joint Symposium "Trends in Artificial Intelligence and Molecular Simulation for Accelerating e-Drug Discovery", Program of the AHeDD2019/IPAB2019 the Joint Symposium, p. 1-2, Nov. 27-29, 2019 & English Abstract.

JPO [Statement of Circumstances Regarding the Accelerated Examination of Japanese Patent Application 2021-023750], Japan Patent Office, JPO, p. 1, Aug. 10, 2021.

Kanagawa Shonan "[Conference Outline for Kanagawa Shonan Health Innovation Park Seminar]", Conference Outline for Kanagawa Shonan Health Innovation Park Seminar, p. 1-2, Nov. 15, 2019 & English Abstract.

Kick-Off Symposium "[Program of the Kick-off Symposium for the Launch of the Computational Medical Science Division]", Kick-off Symposium for the Launch of the Computational Medical Science Division, p. 1-3, Dec. 6, 2019.

Kick-Off Symposium "Cyclic Peptide Drugs", Presentation Materials for the Kick-Off Symposium for the Launch of the Computational Medical Science Division, Tokyo, Japan, p. 1-23, Dec. 6, 2019.

Satoshi et al. "Prediction of Membrane Permeability and Plasma Protein Binding of Cyclic Peptides", Symposium, Tokyo, Japan, 1 P., Nov. 27-29, 2019.

Sugita et al. "Large-Scale Membrane Permeability Prediction of Cyclic Peptides Crossing a Lipid Bilayer Based on Enhanced Sampling Molecular Dynamics Simulations", Journal of Chemical Information and Modeling, 61(7): 3681-3695, Published Online Jul. 8, 2021.

Partial European Search Report and the Provisional Opinion Dated Apr. 4, 2022 From the European Patent Office Re. Application No. 21207727.5. (15 Pages).

Notice of Reason for Refusal Dated Nov. 16, 2021 From the Japan Patent Office Re. Application No. 2021-023750 and Its Translation Into English. (8 Pages).

* cited by examiner

FIG.2

| DATA ID | PEPTIDE INFORMATION | FEATURE INFORMATION | MEMBRANE PERMEABILITY EXPERIMENTAL VALUE | MEMBRANE PERMEABILITY EXPERIMENTAL METHOD | BIOPERSISTENCE EXPERIMENTAL VALUE | BIOPERSISTENCE EXPERIMENTAL METHOD | ANNOTATIONS | PREDICTION INFORMATION | ... |
|---|---|---|---|---|---|---|---|---|---|
| 00001 | a1 | b1 | c1 | d1 | e1 | f1 | g1 | h1 | ... |
| 00002 | a2 | b2 | c2 | d2 | e2 | f2 | g2 | h2 | ... |
| 00003 | a3 | b3 | — | — | e3 | f3 | g3 | h3 | ... |
| 00004 | a4 | b4 | c4 | d4 | — | — | g4 | h4 | ... |
| ... | ... | ... | ... | ... | ... | ... | ... | ... | ... |
| A_00001 | — | b1_A | — | — | e1_A | f1_A | g1_A | h1_A | ... |
| A_00002 | — | b2_A | c2_A | d2_A | e2_A | f2_A | g2_A | h2_A | ... |
| ... | ... | ... | ... | ... | ... | ... | ... | ... | ... |
| B_00001 | — | b1_B | c1_B | d1_B | e1_B | f1_B | g1_B | h1_B | ... |
| ... | ... | ... | ... | ... | ... | ... | ... | ... | ... |

FIG.3

| DATA ID | PEPTIDE INFORMATION | FEATURE INFORMATION | MEMBRANE PERMEABILITY EXPERIMENTAL VALUE | MEMBRANE PERMEABILITY EXPERIMENTAL METHOD | BIOPERSISTENCE EXPERIMENTAL VALUE | BIOPERSISTENCE EXPERIMENTAL METHOD | ANNOTATIONS | PREDICTION INFORMATION | ... |
|---|---|---|---|---|---|---|---|---|---|
| A_00001 | a1_A | b1_A | c1_A | d1_A | e1_A | f1_A | g1_A | h1_A | ... |
| ... | ... | ... | ... | ... | ... | ... | ... | ... | ... |
| ... | ... | ... | ... | ... | ... | ... | ... | ... | ... |

FIG.7

| PEPTIDE ID | STRUCTURAL FORMULA OF PEPTIDE | SMILES CODE | PREDICTION INFORMATION |
|---|---|---|---|
| 00001 | | O=C([C@@H](N1)CC2=CC=C(C=C2)O)N3CCC[C@@H]3C(N[C@H](CC(C)C)C(N[C@H](CC(C)C)C(N[C@@H](CC(C)C)C(N[C@H](CC(C)C)C1=O)=O)=O)=O)=O | ... |
| 00002 | ... | ... | ... |
| ... | ... | ... | ... |

FIG.13

| PEPTIDE WITHOUT RESIDUE MODIFICATION | PREDICTION INFORMATION | SUBSTITUTION CANDIDATE RESIDUE |
|---|---|---|
| (structure) | ... | (structure) |

| CANDIDATE ID | PEPTIDE AFTER RESIDUE MODIFICATION | PREDICTION INFORMATION | INFORMATION OF INTRODUCED RESIDUE |
|---|---|---|---|
| 0001 | (structure) | ... | ... |
| ... | ... | ... | ... |

FIG.15

| USER ID | POINTS | ... |
|---------|--------|-----|
| USER_01 | P_USER_01 | ... |
| ... | ... | ... |
| ... | ... | ... |

INFORMATION PROCESSING DEVICE, INFORMATION PROCESSING METHOD, RECORDING MEDIUM RECORDING INFORMATION PROCESSING PROGRAM, AND INFORMATION PROCESSING SYSTEM

RELATED APPLICATIONS

This application claims the benefit of priority of Japan Patent Application Nos. 2021-023750 filed on Feb. 17, 2021 and 2020-189856 filed on Nov. 13, 2020. The contents of the above applications are all incorporated by reference as if fully set forth herein in their entirety.

FIELD AND BACKGROUND OF THE INVENTION

The present disclosure relates to an information processing device, an information processing method, a recording medium recording an information processing program, and an information processing system.

RELATED ART

Japanese Patent Application Laid-Open (JP-A) No. 2017-037378 (for example, claim 4 thereof) discloses, in structural analysis of a biopolymer, clustering plural structures in a multidimensional space whose coordinate axes correspond to all of index dimensions included in a dimensional assembly, and conducting a molecular dynamics simulation in which an initial structure is a structure with an outlier value that is not included in any of the clusters.

International Patent Publication No. 2003/054743 discloses a protein stereostructure prediction program that predicts the stereostructure of a protein. A computer executing the protein stereostructure prediction program reads an amino acid sequence of the protein and predicts two-dimensional structural information. The computer then calculates numbers of the amino acids constituting the protein on the basis of the two-dimensional structure information. From the calculated numbers of amino acids and the two-dimensional structural information, the computer acquires turn structure information of turns with high probabilities of occurrence, predicts and reproduces the turns, and thus predicts the stereostructure of the protein.

Japanese Patent Application National Publication No. 2020-523010 (for example, claim 1 thereof) discloses a method of inputting respective peptide sequences of a set of neoantigens into a machine learning-trained suggestion model, and thus generating, for each of patients, a set of numerical suggestion likelihoods for the set of neoantigens in the patient.

Japanese Patent Application National Publication No. 2020-519246 (for example, claim 1 thereof) discloses a method of using a processor of a computer to input numerical vectors of peptides into a deep learning-trained suggestion model, and thus generating a set of suggestion likelihoods for a set of neoantigens.

In recent years, peptide drugs have attracted attention among medium molecule drugs. However, there is much that is unclear about the pharmacokinetics of peptides.

The technologies disclosed in the above-mentioned JP-A No. 2017-037378, International Patent Publication No. 2003/054743, and Japanese Patent Application National Publication Nos. 2020-523010 and 2020-519246 are a technology that runs a molecular dynamics simulation of a biopolymer, a technology that predicts the stereostructure of a protein with a computer, and technologies that predict peptides that will be effective against neoantigens; these technologies do not predict pharmacokinetics of peptides. Therefore, the technologies of these references may not predict pharmacokinetics of peptides.

In consideration of the circumstances described above, an object of the present disclosure is to predict pharmacokinetics of peptides.

SUMMARY OF THE INVENTION

A first aspect of the present disclosure is an information processing device including: a reception section that receives request signals transmitted from a terminal; a prediction section that generates prediction information relating to pharmacokinetics of a peptide in response to the request signals; and a transmission section that transmits the prediction information generated by the prediction section to the terminal.

A second aspect of the present disclosure is an information processing method causing a computer to execute processing including: receiving request signals transmitted from a terminal; generating prediction information relating to pharmacokinetics of a peptide in response to the request signals; and transmitting the generated prediction information to the terminal.

A third aspect of the present disclosure is a recording medium recording an information processing program that causes a computer to execute processing including: receiving request signals transmitted from a terminal; generating prediction information relating to pharmacokinetics of a peptide in response to the request signals; and transmitting the generated prediction information to the terminal.

A fourth aspect of the present disclosure is an information processing system including a terminal and an information processing device, wherein: the terminal transmits request signals to the information processing device; the information processing device receives the request signals transmitted from the terminal, generates prediction information relating to pharmacokinetics of a peptide in response to the request signals, and transmits the generated prediction information to the terminal; and the terminal displays the prediction information transmitted from the information processing device at a display unit.

According to the present disclosure, an effect is provided in that pharmacokinetics of peptides may be predicted.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF THE SEVERAL VIEWS OF THE DRAWINGS

FIG. 2 is a diagram describing an example of data stored in a shared database 142.

FIG. 3 is a diagram describing an example of data stored in a user database 144.

FIG. 7 is an image showing an example of a screen displayed at a display unit of a terminal.

FIG. 13 is a diagram showing an example of design assistance information.

FIG. 15 is a diagram showing an example of a table stored in a compensation memory section.

DESCRIPTION OF SPECIFIC EMBODIMENTS OF THE INVENTION

Below, exemplary embodiments of the present invention are described in detail with reference to the attached drawings.

First Exemplary Embodiment

—Structure of Information Processing System—

Figure 1:
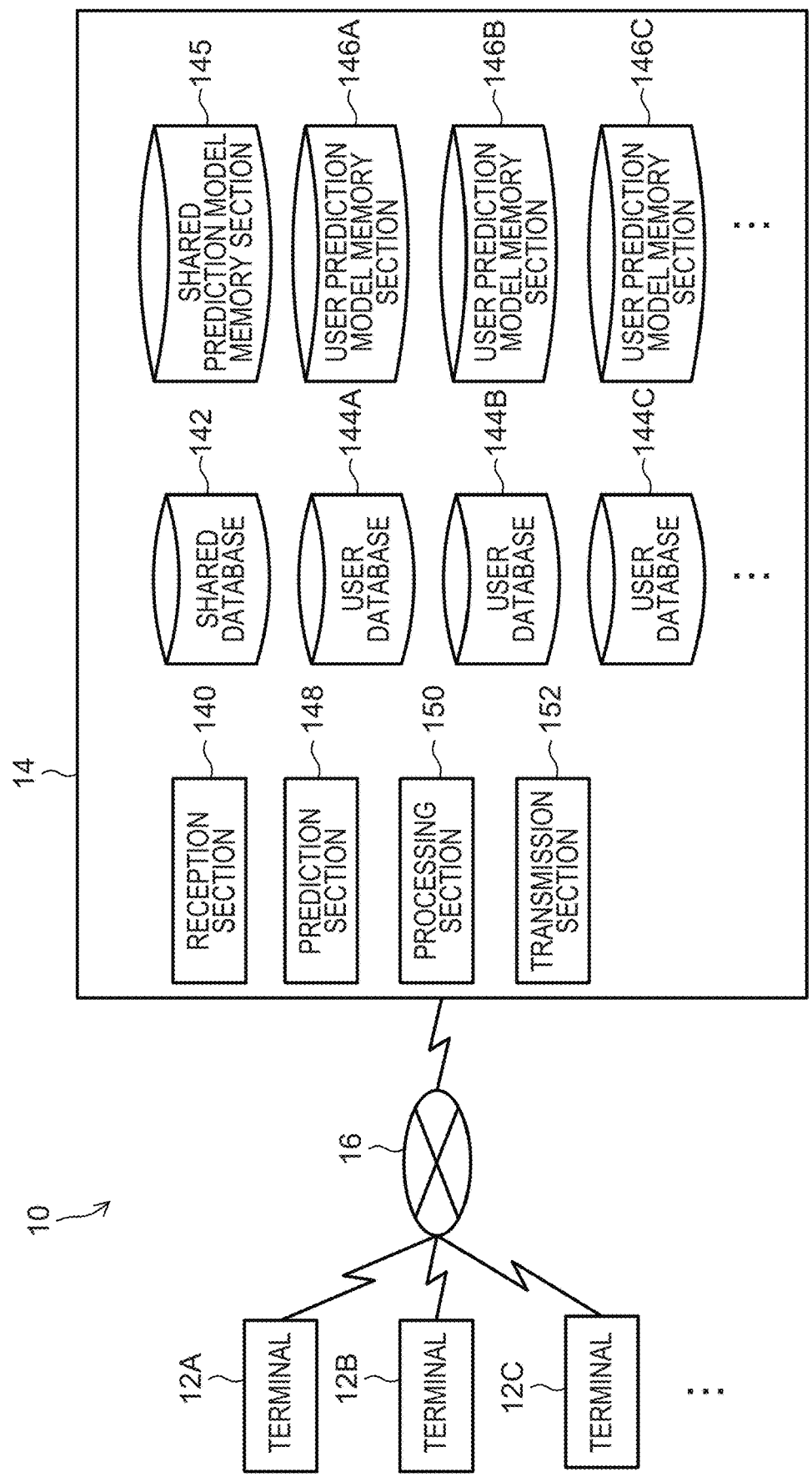
FIG. 1 is a block diagram showing an information processing system according to a first exemplary embodiment.

FIG. 1 is a block diagram showing an example of structures of an information processing system 10 according to a first exemplary embodiment. In functional terms, as shown in FIG. 1, the information processing system 10 is provided with plural terminals 12A, 12B and 12C and a server 14, which is an example of an information processing device. The plural terminals 12A, 12B and 12C and the server 14 are connected via a network 16 such as, for example, the Internet or the like. Below, when an individual terminal is being referred to, the terminal is denoted simply as the terminal 12. In FIG. 1, the plural terminals 12A, 12B and 12C are illustrated as an example; the information processing system 10 may be provided with a greater or smaller number of terminals.

—Terminals—

The respective plural terminals 12A, 12B and 12C are operated by plural different users. Each user enters peptide information representing a peptide that the user wants to analyze into the terminal 12 that the user is operating. The user then operates the terminal 12 so as to transmit the peptide information to the server 14, which is described below, and the terminal 12 transmits the peptide information entered by the user through the network 16 to the server 14. The peptide information includes information of one or more of a peptide structural formula, a peptide SMILES code, a peptide primary structure, a peptide secondary structure, a peptide tertiary structure and a peptide quaternary structure.

—Server—

As shown in FIG. 1, the server 14 is provided with a reception section 140, a shared database 142, plural user databases 144A, 144B and 144C, a shared prediction model memory section 145, plural user prediction model memory sections 146A, 146B and 146C, a prediction section 148, a processing section 150 and a transmission section 152.

Below, when an individual user database is being referred to, the user database is denoted simply as the user database 144, and when an individual user prediction model memory section is being referred to, the user prediction model memory section is denoted simply as the user prediction model memory section 146. In FIG. 1, the plural user databases 144A, 144B and 144C are illustrated as an example; the server 14 may be provided with a greater or smaller number of user databases. Similarly, in FIG. 1 the plural user prediction model memory sections 146A, 146B and 146C are illustrated as an example; the server 14 may be provided with a greater or smaller number of user prediction model memory sections.

The reception section 140 receives request signals transmitted from the terminal 12, including a user ID identifying the terminal, peptide information and prediction model selection information, which is described below.

The shared database 142 stores data of an administrator administering the server 14 and data of the users operating the terminals 12. FIG. 2 shows an example of data stored in the shared database 142. As shown in FIG. 2, data IDs are assigned to the data. Each data ID is identification information for identifying the data. The data IDs are also for identifying whether data is from the administrator or from a user.

As illustrated in FIG. 2, the data corresponding to data IDs 00001 to 00004 and so forth is data from the administrator. This data associates and stores peptide information, feature information of the peptide information, an experimental value of membrane permeability of the peptide, an experimental method used to obtain the experimental value of membrane permeability of the peptide, an experimental value of biopersistence of the peptide, an experimental method used to obtain the experimental value of biopersistence of the peptide, annotations, and prediction information generated by the prediction section 148, which is described below. The value of biopersistence of the peptide is, for example, a plasma protein binding rate of the peptide. The annotations include information representing how the data has been obtained and the like. The annotations field may also store a score representing credibility of the data. The data corresponding to data IDs 00001 to 00004 is stored in the shared database 142 by the administrator of the server 14 in advance.

As illustrated in FIG. 2, the data corresponding to data IDs A_00001, A_00002, B_00001 and so forth is data from users. This data is not associated with peptide information but associates and stores feature information of peptide information, an experimental value of membrane permeability of the peptide, an experimental method used to obtain the experimental value of membrane permeability of the peptide, an experimental value of biopersistence of the peptide, an experimental method used to obtain the experimental value of biopersistence of the peptide, annotations, and prediction information generated by the prediction section 148 described below. The data corresponding to the data IDs A_00001, A_00002, B_00001 and so forth is stored in the shared database 142, subject to agreement by the users.

Data from the users is stored in the plural user databases 144A, 144B and 144C. FIG. 3 shows an example of data stored in the user database 144. As illustrated in FIG. 3, the user database 144 associates and stores peptide information, feature information of the peptide information, an experimental value of membrane permeability of the peptide, an experimental method used to obtain the experimental value of membrane permeability of the peptide, an experimental value of biopersistence of the peptide, an experimental method used to obtain the experimental value of biopersistence of the peptide, annotations, and prediction information generated by the prediction section 148 described below. Some or all of this data may be omitted from the data stored in the user database 144.

As described above, peptide information in data from a user is not stored in the shared database 142 but the peptide information is stored in the user database 144. Because peptide information is highly confidential information, it is likely that users would be resistant to their peptide information being stored in the shared database 142 that stores data from other users and the administrator.

Accordingly, in the present exemplary embodiment, the user database 144 that is different from the shared database 142 is provided and peptide information from the user is stored only in the user database 144. In contrast, the peptide information from the user is not stored in the shared database 142.

The feature information obtained from peptide information is vector expression information composed of collections of many numerical values computed by reversible or irreversible arithmetic processing, focusing on various local structures or overall structure of the peptide. The feature information is lower in confidentiality than the peptide information. Therefore, it is likely that there will be users who consider storing the feature information in the shared database 142 to be acceptable.

Accordingly, in the present exemplary embodiment, the shared database 142 stores information relating to the feature information. This information stored in the shared database 142 is used in creation of a prediction model for predicting membrane permeability or biopersistence of peptides, or the like. The prediction models are described below. The information stored in the shared database 142 is treated as information that may be utilized by the administrator administering the server 14. Moreover, the information stored in the shared database 142 is treated as information that may be utilized by all users as well as the administrator. Some of the information stored in the shared database 142 may be specified to be information that users may not utilize.

The shared prediction model memory section 145 stores prediction models.

Each of the plural user prediction model memory sections 146A, 146B and 146C stores prediction models for the user.

Figure 4:
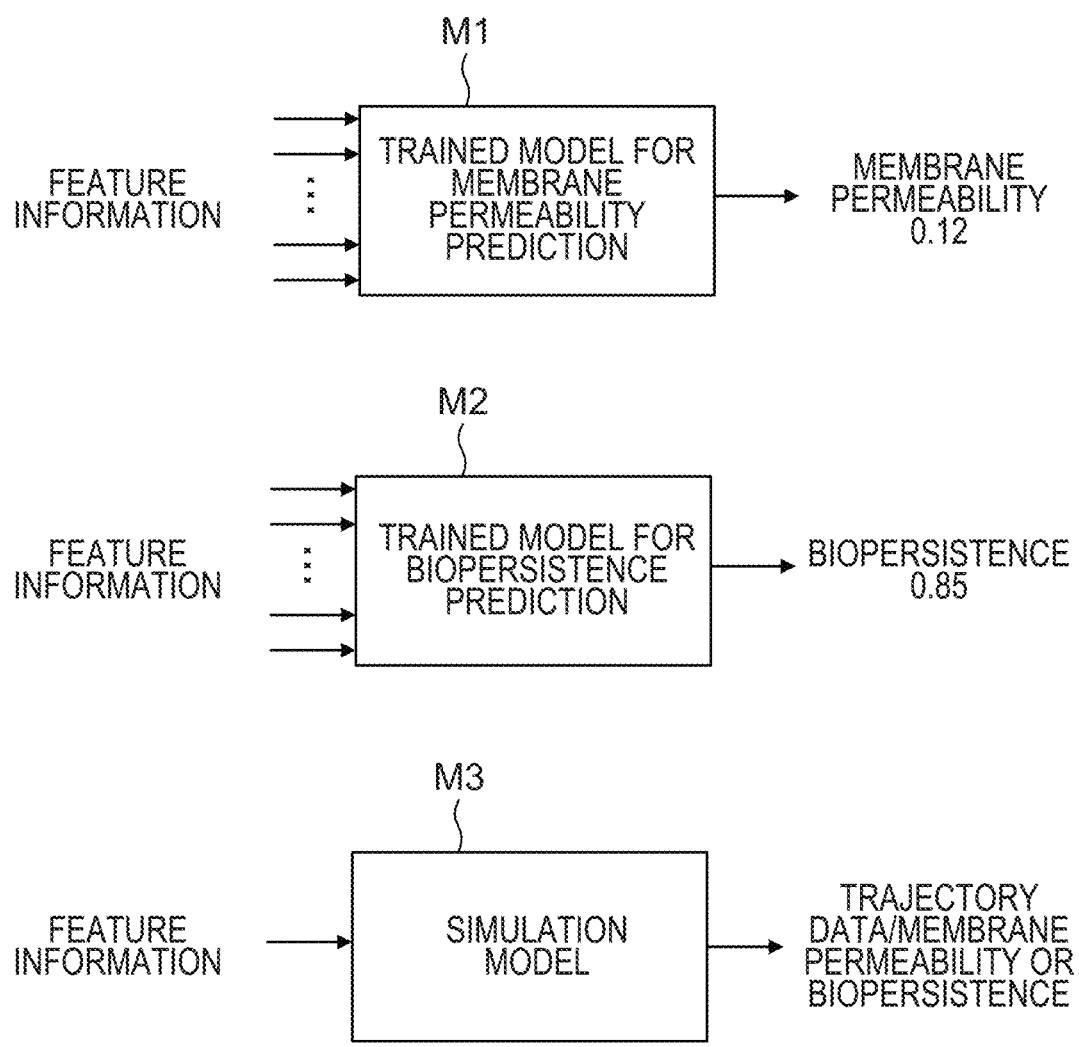
FIG. 4 is a diagram describing prediction models of the present exemplary embodiment.

FIG. 4 shows examples of prediction models according to the present exemplary embodiment. The examples of prediction models shown in FIG. 4 are a trained model for membrane permeability prediction M1, a trained model for biopersistence prediction M2, and a simulation model M3 for running a molecular dynamics simulation relating to pharmacokinetics of the peptide. As shown in FIG. 4, when feature information obtained from peptide information is inputted into the trained model for membrane permeability prediction M1, the model outputs a prediction value of membrane permeability for the peptide. When feature information obtained from peptide information is inputted into the trained model for biopersistence prediction M2, the model outputs a prediction value of biopersistence for the peptide. When peptide information is inputted into the simulation model M3, the simulation model M3 outputs trajectory data of a molecular dynamics simulation relating to pharmacokinetics of the peptide. The data outputted from the simulation model M3 is trajectory data, but statistical analysis or the like may be applied to the trajectory data, a prediction value of membrane permeability or biopersistence of the peptide may be calculated, and the simulation model M3 may output this value.

The trained models are created using all or some of the data stored in the shared database 142 or user database 144 as training data. More specifically, the experimental values associated with the feature information are used as teaching data, and the trained models are created by machine learning with teaching. The trained models are realized by, for example, neural networks (including, for example, deep learning networks that are trained by deep learning), support vector machines and the like. The trained models are not limited to these kinds of machine learning models and may be realized by techniques such as logistic regression and the like.

The shared prediction model memory section 145 stores a trained model, which is created using data stored in the shared database 142 as training data, and a simulation model as the prediction models. Meanwhile, each of the plural user prediction model memory sections 146A, 146B and 146C stores a trained model, which is created using data stored in the user database 144 as training data, and a simulation model, which is prepared for the respective user, as the prediction models.

When the activity of peptides is to be predicted, it is likely that a user A intends to analyze the activity of peptides of one kind and another user B intends to analyze the activity of peptides of another kind. Because the data stored in the user database 144 for each user is different, it is likely that optimum methods of construction of the prediction models are different. Accordingly, in the present exemplary embodiment prediction models that predict the pharmacokinetics of peptides are prepared for the respective users.

More specifically, prediction models for user A are stored in the user prediction model memory section 146A, prediction models for user B are stored in the user prediction model memory section 146B, and prediction models for user C are stored in the user prediction model memory section 146C. Thus, prediction models corresponding to the peptides that the users intend to analyze are prepared, and the users may utilize these prediction models to obtain prediction information of peptides.

It is conceivable that a user wants to predict the pharmacokinetics of a peptide using a general prediction model rather than a separate prediction model created from that user's data. Accordingly, in the present exemplary embodiment the shared prediction model memory section 145 stores the trained model created using the data stored in the shared database 142 as training data, and a standard simulation model.

Therefore, when prediction model selection information that is included in request signals transmitted from the terminal 12 indicates a prediction model stored in the user prediction model memory section 146, in accordance with a user ID received by the reception section 140, the prediction section 148 reads the prediction model from the user prediction model memory section 146 corresponding to that user ID.

Alternatively, when prediction model selection information that is included in request signals transmitted from the terminal 12 indicates a prediction model stored in the shared prediction model memory section 145, the prediction section 148 reads the prediction model from the shared prediction model memory section 145.

The prediction section 148 converts peptide information received by the reception section 140 to feature information by a previously known technique. Then, the prediction section 148 generates prediction information corresponding to the peptide information by inputting one or both of the peptide information and the feature information into the prediction model that has been read.

For example, when the prediction model is the trained model for membrane permeability prediction M1, a prediction value of membrane permeability is generated as the prediction information. When the prediction model is the trained model for biopersistence prediction M2, a prediction value of biopersistence is generated as the prediction information. When the prediction model is the simulation model M3, the prediction section 148 inputs the peptide information received by the reception section 140 into the simulation model M3, simulating activity of the peptide in the body by a previously known molecular dynamics simulation process. Thus, prediction information relating to pharmacokinetics of a peptide is generated.

The shared prediction model memory section 145 and the user prediction model memory section 146 may store plural prediction models that generate the same kind of prediction information. For example, the user prediction model memory section 146 may store plural trained models for membrane permeability production, and the user prediction model memory section 146 may store plural simulation models.

For example, a situation is anticipated in which a user generates prediction information of a peptide using each of a trained model for membrane permeability prediction X and a trained model for membrane permeability prediction Y, which are stored in the user prediction model memory section 146, and a trained model for membrane permeability prediction Z and a trained model for membrane permeability prediction W, which are stored in the shared prediction model memory section 145. Similar situations are anticipated for trained models for biopersistence prediction and for simulation models.

In this kind of situation, plural prediction models of the same kind may be used to generate plural sets of prediction information from one set of peptide information. In this situation, for example, the prediction information generated by each of the plural prediction models of the same kind may be checked to investigate which prediction information is appropriate. Alternatively, the prediction information generated by each of the plural prediction models of the same kind may be averaged or the like to obtain appropriate prediction information. In this situation, plural sets of prediction information may be generated by performing the processing to generate feature information from the peptide information that is the object of prediction one time and inputting the generated feature information into the plural prediction models.

The shared prediction model memory section 145 stores various parameters for generating prediction information. These various parameters are used when using a prediction model to generate prediction information. The plural user prediction model memory sections 146A, 146B and 146C also store various parameters for generating prediction information, and these various parameters differ between users. Because the various parameters for generating prediction information differ from user to user, prediction information may be generated that is suitable according to the wishes of the users. Plural numbers of various parameters of the same kind may be stored in the shared prediction model memory section 145 or the user prediction model memory section 146. When obtaining prediction information of a peptide, the user suitably selects parameters that the user thinks suitable from these various parameters, and prediction information of the peptide is generated at the server 14.

The processing section 150 associates the peptide information received by the reception section 140 with the feature information and prediction information obtained by the prediction section 148, and stores the information in the user database 144 corresponding with the user ID.

The transmission section 152 transmits the prediction information generated by the prediction section 148 to the terminal 12 corresponding to the user ID received by the reception section 140.

The terminal 12 receives the prediction information transmitted from the server 14 and displays the prediction information at a display unit (not shown in the drawings).

Figure 5:
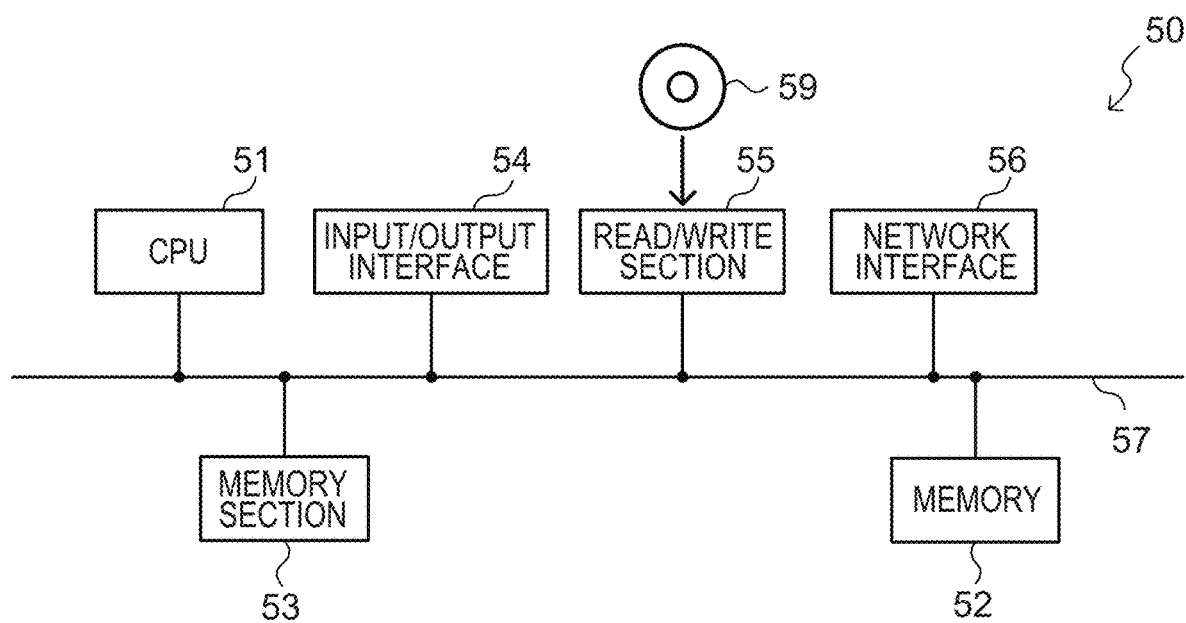
FIG. 5 is a diagram showing a computer that realizes each of devices of an information processing system.

The terminals 12 and the server 14 may each be realized by, for example, a computer 50 as illustrated in FIG. 5. The computer 50 that realizes the terminal 12 or server 14 is provided with a CPU 51, a memory 52 that serves as a temporary memory area, and a nonvolatile memory section 53. The computer is further provided with an input/output interface 54 that is connected to input/output devices and the like (not shown in the drawings) and with a read/write section 55 that controls reading and writing of data at a recording medium 59. The computer is also provided with a network interface 56 that is connected to a network such as the Internet or the like. The CPU 51, memory 52, memory section 53, input/output interface 54, read/write section 55 and network interface 56 are connected to one another via a bus 57.

The memory section 53 may be realized by a hard disk drive (HDD), solid state drive (SSD), flash memory or the like. A program causing the computer to function as the terminal 12 or server 14 is stored at a memory medium serving as the memory section 53. The CPU 51 reads the program from the memory section 53 and loads the program into the memory 52, and successively executes processes included in the program.

Now, operation of the information processing system 10 according to the exemplary embodiment is described.

Figure 6:
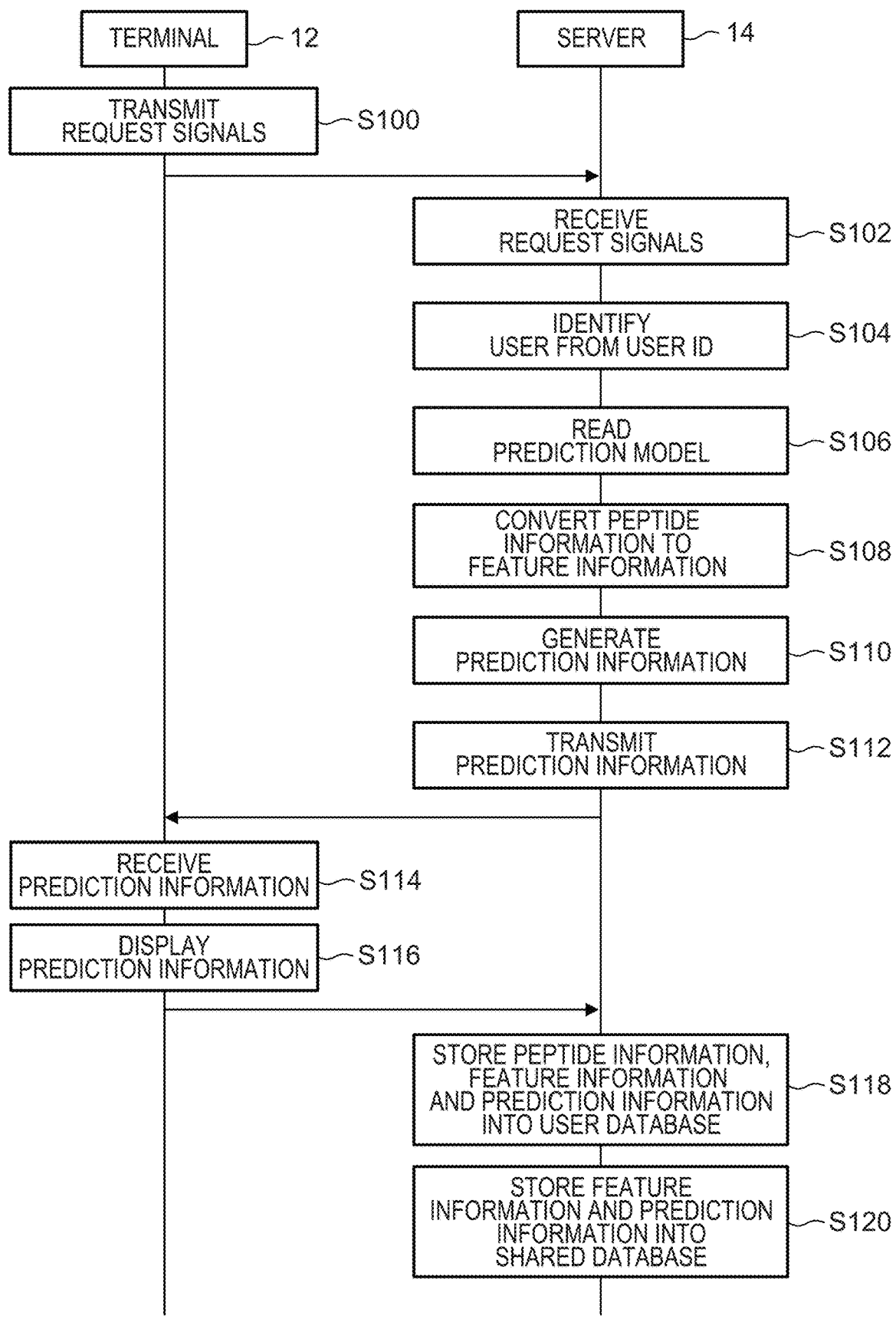
FIG. 6 is a sequence that is executed in the information processing system.

When a user operating the terminal 12 enters peptide information of an object of prediction into the terminal 12 and performs operations to transmit the peptide information to the server 14, a sequence as illustrated in FIG. 6 is executed. More specifically, the sequence as illustrated in FIG. 6 is executed when the user operating the terminal 12 enters the peptide information of the object of prediction into the terminal 12, sends the peptide information to the server 14, and sends command signals commanding a prediction of activity of the peptide by a trained model to the server 14. The sequence in FIG. 6 is an example describing a situation in which a single prediction model is selected and prediction information is generated by that prediction model. In another situation, prediction information may be generated by each of plural prediction models as described above, in which case information designating the plural prediction models is included in the prediction model selection information, which is described below.

In step S100, the terminal 12 transmits to the server 14 request signals including peptide information entered by the user and the user's user ID. The request signals include the prediction model selection information indicating whether prediction information is to be generated using a prediction model of the user stored in the user prediction model memory section 146 or prediction information is to be generated using a prediction model stored in the shared prediction model memory section 145.

In step S102, the reception section 140 of the server 14 receives the request signals transmitted from the terminal 12 in step S100.

In step S104, the prediction section 148 of the server 14 identifies the user of the terminal 12 from the user ID included in the request signals received in step S102.

In step S106, on the basis of the prediction model selection information included in the request signals received in step S102, the prediction section 148 of the server 14 makes a determination as to which prediction model is to be used for generating prediction information. When the selection information indicates utilization of a prediction model of the user, the prediction section 148 of the server 14 reads the prediction model from the user prediction model memory section 146 corresponding with the user ID. Alternatively, when the prediction model selection information indicates utilization of a prediction model in the shared prediction model memory section 145, the prediction section 148 of the server 14 reads the prediction model from the shared prediction model memory section 145.

In step S108, the prediction section 148 of the server 14 converts the peptide information included in the request signals received in step S102 to feature information.

In step S110, the prediction section 148 of the server 14 generates prediction information of the peptide by inputting the feature information obtained in step S108 into the prediction model read in step S106.

In step S112, the transmission section 152 of the server 14 transmits the prediction information obtained in step S110 to the terminal 12. The transmission section 152 may associate and transmit to the terminal 12 the prediction information obtained in step S110 with peptide information of the object of prediction (for example, a structural formula of the peptide or the like).

In step S114, the terminal 12 receives the prediction information transmitted in step S112.

In step S116, the terminal 12 displays the prediction information received in step S114 at the display unit (not shown in the drawings).

In this case, as illustrated in FIG. 7, the display unit (not shown in the drawings) of the terminal 12 displays information representing the structural formula of the peptide, the SMILES code of the peptide, and the prediction information. FIG. 7 is an example of information in which the prediction information of the peptide is associated with the structural formula of the peptide that is the object of prediction.

The object of prediction may be plural peptides rather than a single peptide, in which case, for each of the plural peptides, the peptide information (for example, information representing the structural formula of the peptide), the SMILES code of the peptide and the prediction information are displayed at the display unit (not shown in the drawings) of the terminal 12. In this situation, the processing of step S106 to step S110 is repeated for each of the plural sets of peptide information, and the prediction information for each of the plural sets of peptide information is displayed at the display unit (not shown in the drawings) of the terminal 12. When plural prediction models are read in step S106, the prediction information for one set of peptide information is generated by the plural prediction models.

Thus, the user may obtain prediction information relating to pharmacokinetics of the peptide simply by operating that user's terminal 12.

In step S118, the processing section 150 of the server 14 associates the peptide information included in the request signals received in step S102, the feature information obtained in step S108 and the prediction information generated in step S110, and stores this information into the user database 144 corresponding with the user ID.

In step S120, the processing section 150 of the server 14 stores the feature information obtained in step S108 and the prediction information generated in step S110 into the shared database 142.

Figure 8:
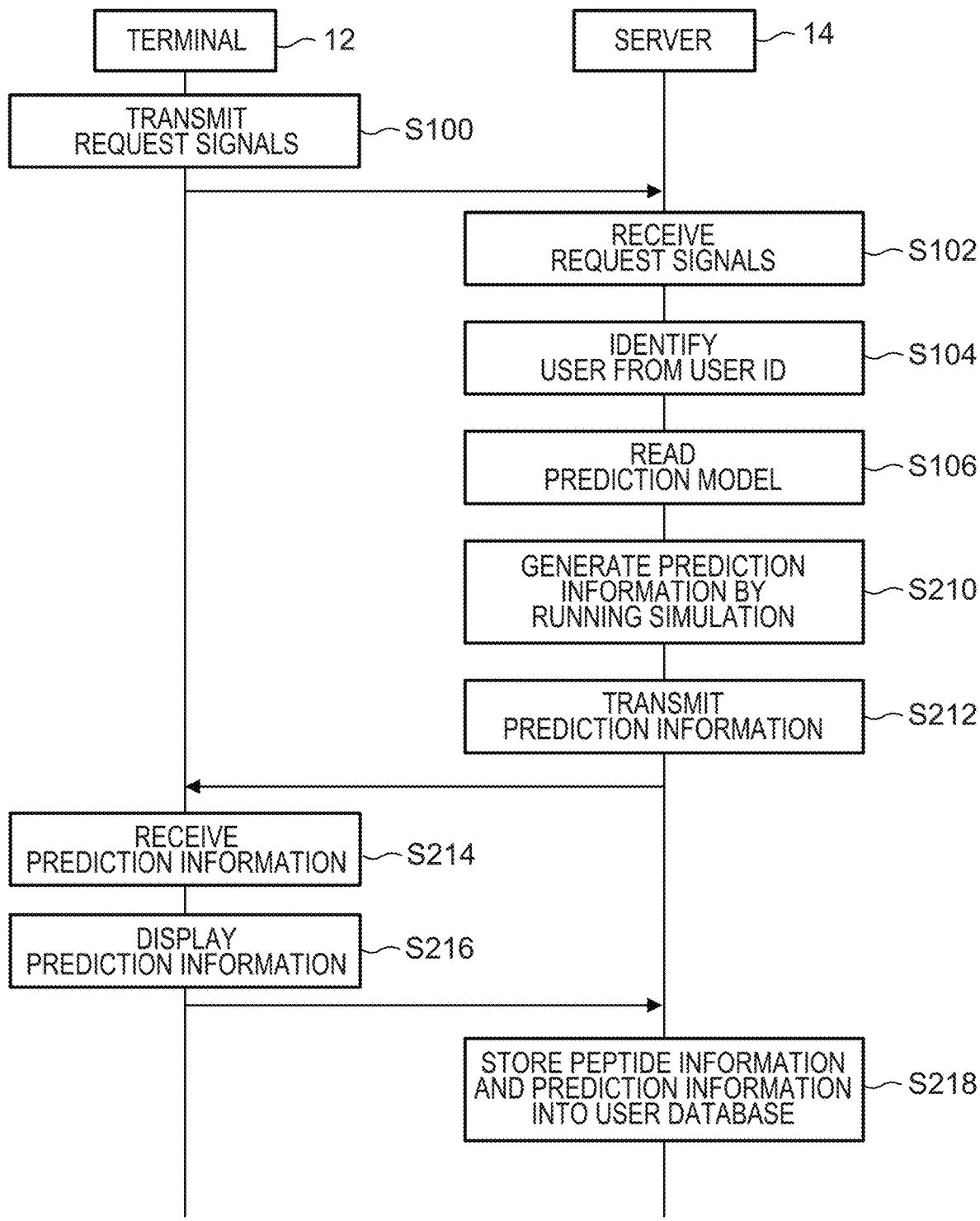
FIG. 8 is a sequence that is executed in the information processing system.

When a user operating the terminal 12 enters peptide information of an object of prediction into the terminal 12, sends the peptide information to the server 14, and sends command signals to the server 14 commanding a prediction of activity of the peptide by a molecular dynamics simulation, a sequence as illustrated in FIG. 8 is executed.

Step S100 to step S106 shown in FIG. 8 are similar to those steps in FIG. 6.

In step S210, the prediction section 148 of the server 14 inputs the peptide information received in step S102 into a simulation model serving as the prediction model, and activity of the peptide in the body is simulated by a previously known molecular dynamics simulation process. Thus, prediction information relating to pharmacokinetics of the peptide is generated.

In step S212, the prediction section 148 of the server 14 transmits the prediction information generated in step S210 to the terminal 12.

In step S214, the terminal 12 receives the prediction information transmitted from the server 14 in step S212.

In step S216, the terminal 12 displays the prediction information received in step S214 at the display unit (not shown in the drawings).

In step S218, the processing section 150 of the server 14 associates the peptide information included in the request signals received in step S102 with the prediction information generated in step S210 and stores this information into the user database 144 corresponding with the user ID.

The prediction information of the peptide in this case is, for example, at least one of trajectory data simulating movements of the peptide molecule in a time series, a prediction value of membrane permeability or biopersistence that is obtained by applying a statistical analysis to trajectory data or the like, and suchlike. Activity relating to membrane probability, biopersistence or the like of the peptide may be visualized with video images based on the trajectory data.

As is described in detail above, the server of the information processing system generates prediction information relating to pharmacokinetics of a peptide in response to request signals transmitted from a terminal, and the server transmits the prediction information to the terminal. Thus, the server may predict pharmacokinetics of the peptide.

The present disclosure is not limited by the exemplary embodiments described above; various modifications and applications are possible within a scope not departing from the gist of the disclosure.

For example, an example is described in which the server 14 according to the exemplary embodiment described above predicts membrane permeability and biopersistence as the prediction information of pharmacokinetics of a peptide, but this is not limiting. Any kind of information of pharmacokinetics of a peptide may be predicted. For example, a physical parameter such as blood-brain barrier permeability, solubility of the peptide in the body's internal environment or the like may be predicted as pharmacokinetics of a peptide.

Figure 9:
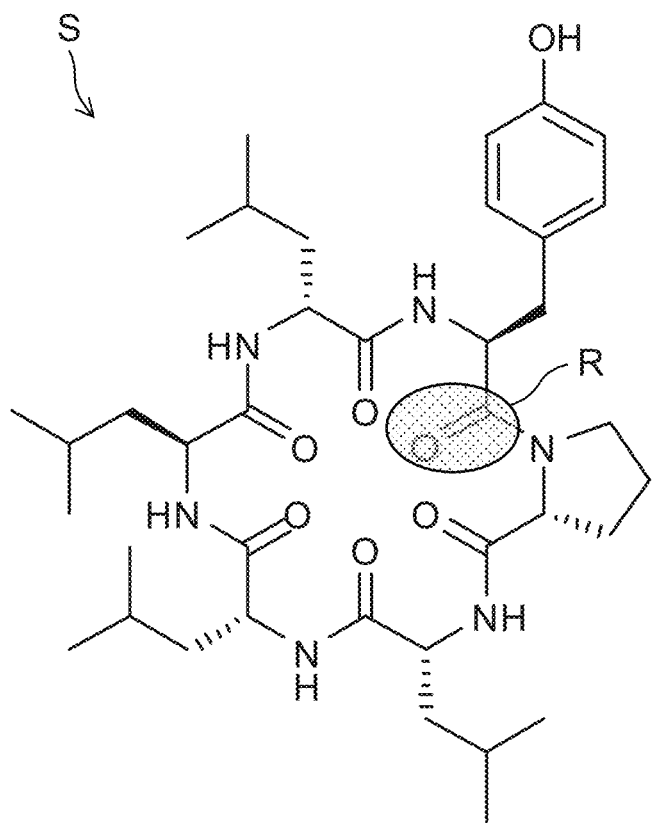
FIG. 9 is a diagram showing an example of design assistance information.

Further, an example is described in which the server 14 according to the exemplary embodiment described above generates only prediction information of a peptide, but this is not limiting. For example, with the object of improving pharmacokinetics of a peptide, the server 14 may be further provided with a design assistance section that generates design assistance information indicating modification site candidates among elements structuring the peptide. For example, residues of a peptide may be mentioned as the elements structuring the peptide. In this configuration, the server 14 generates, for example, design assistance information S including a modification site candidate R. The design assistance information S is displayed, as illustrated in FIG. 9, at the display unit of the terminal 12. Thus, design of a peptide by the user is assisted. The server 14 may generate only design assistance information of a peptide instead of prediction information of the peptide, and transmit this design assistance information to the terminal 12.

In the exemplary embodiment described above, an example is described in which feature information and prediction information are stored in the shared database 142 and peptide information, feature information and prediction information are stored in the user database 144. However, numerous variant examples relating to information storage can be anticipated.

For example, in the exemplary embodiment described above, an example is described in which all feature information and prediction information of peptide information transmitted to the server 14 by users as objects of prediction are stored in the shared database 142, but this is not limiting.

For example, of feature information and prediction information of peptide information, the server 14 may store feature information and prediction information in the shared database 142 only with the agreement of the user. For example, when feature information and prediction information are to be stored in the shared database 142 in step S120 of FIG. 6, the server 14 outputs confirmation signals to the terminal 12 regarding whether the feature information may be stored in the shared database 142. When the terminal 12 receives the confirmation signals transmitted from the server 14, the terminal 12 displays a screen at the display unit (not shown in the drawings) of the terminal 12 to obtain confirmation as to whether the feature information of the peptide information that is the object of prediction may be stored in the shared database 142. At this time, for example, a display is displayed at the display unit (not shown in the drawings) of the terminal 12 indicating that if the user agrees to storage of the feature information in the shared database 142, then the feature information or prediction information can be used when generating prediction information of peptides for other users and that the user will be awarded points or the like as compensation for the provision of the feature information or prediction information. When, for example, the user performs an entry operation at the terminal 12 indicating that the feature information or prediction information may be stored in the shared database 142, the terminal 12 transmits command signals indicating the same to the server 14. On the other hand, when the user performs an entry operation at the terminal 12 indicating that the user does not agree to storing the feature information or prediction information in the shared database 142, the terminal 12 transmits command signals indicating the same to the server 14.

In response to the command signals received from the terminal 12, the server 14 makes a determination as to whether or not to store the feature information or prediction information in the shared database 142. If the command signals transmitted from the terminal 12 indicate agreement to storage of the feature information or prediction information in the shared database 142, then the server 14 stores the feature information or prediction information in the shared database 142. On the other hand, if the command signals received from the terminal 12 indicate no agreement to storing the feature information or prediction information in the shared database 142, then the server 14 ends the processing without storing the feature information or prediction information in the shared database 142. Thus, because data is recorded in accordance with the intentions of users, use of the server 14 by users is facilitated. As described above, when feature information or prediction information is provided from a user and the feature information or prediction information is stored in the shared database 142, points can be awarded to the user. The points awarded to the user can be used, for example, for discounting usage fees for use of the server 14 or the like.

After a user receives prediction information of a peptide, the user may perform experiments to verify how activity of the peptide is actually manifested in the body. The user may confirm experimental values and store the experimental values in the user database 144 and shared database 142 of the server 14. Similarly to the feature information and prediction information as described above, if a user agrees to storing experimental values and information on experimental methods in the shared database 142, and these various kinds of information obtained by experiment by the user are then stored in the shared database 142, points or the like are awarded to the user as compensation for the provision of the various kinds of information obtained by experiment. Hence, the experimental values obtained by experiment by the user are information that may be employed by other users and the administrator of the server 14 and may, for example, be employed by a user or the administrator as teaching data in machine learning of a prediction model. For example, the values $c2\_A$, $d2\_A$, $e2\_A$ and $f2\_A$ shown in FIG. 2 are an example of experimental information provided from a user. When this experimental information is stored in the shared database 142, points are awarded to the user.

When data is to be stored in the various memory sections of the server 14, a user may select a mode of not storing data at the server 14 at all, storing data only in the user database 144, or also storing data in the shared database 142.

When points are to be awarded to a user, the administrator of the server 14 may award points to the user in accordance with an activity history of the user, a credibility value stored in the annotations illustrated in FIG. 2 or the like, and so forth. The credibility stored in the annotations or the like may be either credibility of the data provided by the user or credibility of the user. In these cases, more points are awarded to a user providing higher-quality data or to a user with higher credibility.

In the exemplary embodiment described above, an example is described in which the trained models that are stored in each of the plural user prediction model memory sections 146A, 146B and 146C are trained models created using only data stored in the user database 144 as training data, but this is not limiting. For example, the trained models stored in each of the plural user prediction model memory sections 146A, 146B and 146C may be created using, in addition to the data stored in the user database 144, data stored in the shared database 142 as training data. More specifically, a trained model may be created using some or all of the data stored in the shared database 142 as training data in addition to the data stored in the user database 144. Thus, a trained model with higher prediction accuracy may be created. In this case, the various kinds of data to be used as training data may be registered in advance in the user database 144 or the shared database 142.

As well as a user providing data by storing various kinds of data in the shared database 142 of the server 14 as described above, a user may provide a prediction model created by the user to the server 14. In this case, similarly to the above descriptions, points are awarded to the user when the prediction model is provided.

Data stored in the shared database 142 or the user database 144 may be downloadable to the terminal 12. Further, data stored in the shared database 142 or the user database 144 may be in a condition that allows editing by the terminal 12. In this case, data that is editable from the terminal 12 may be subject to restrictions. For example, the data stored in the shared database 142 may be configured such that editing thereof from the terminal 12 is not possible. The terminal 12 or the server 14 may employ data stored in the shared database 142 or the user database 144 to generate various kinds of information relating to pharmacokinetics of peptides. For example, the terminal 12 or the server 14 may generate various kinds of information relating to pharmacokinetics of peptides, such as a graph in which the horizontal axis represents a feature quantity of peptides (for example, lipid solubility) and the vertical axis represents membrane permeability, and so forth.

In the exemplary embodiment described above, an example is described in which the prediction section 148 of the server 14 converts peptide information included in request signals transmitted from the terminal 12 to feature information, but this is not limiting. For example, feature information may be included in request signals transmitted from the terminal 12.

Users utilizing services provided by the server 14 are expected to include users who are reluctant to transmit peptide information such as a structural formula or the like of a peptide to the server 14. Accordingly, a conversion from peptide information to feature information may be executed in advance by, for example, the terminal 12 that the user is operating or a different computer from the server 14, and this feature information may be included in the request signals. In this case, the terminal 12 transmits request signals to the server 14 including the feature information that has been converted from the peptide information. The reception section 140 of the server 14 receives the request signals transmitted from the terminal 12. The prediction section 148 of the server 14 generates prediction information of the peptide by inputting the feature information included in the request signals into a prediction model. The transmission section 152 of the server 14 then transmits the obtained prediction information to the terminal 12. Thus, a user may obtain prediction information of a peptide without transmitting peptide information that is a structural formula of the peptide or the like to the server 14. However, a simulation model may not be selected as the prediction model in this case, because peptide information such as a structural formula of the peptide or the like is necessary for prediction by a simulation model. For example, a conversion program or the like for converting from peptide information to feature information is employed by the server 14 or a computer different from the server 14. A measure such as providing the terminal 12 or computer different from the server 14 with the conversion program in advance or the like is anticipated.

Second Exemplary Embodiment

Now, a second exemplary embodiment is described. An information processing system according to the second exemplary embodiment assists design of a peptide by a user. The second exemplary embodiment is described in more concrete detail than the first exemplary embodiment. Structures of the information processing system according to the second exemplary embodiment that are similar to parts of the information processing system according to the first exemplary embodiment are assigned the same reference symbols and are not described here.

When a user is designing a peptide, the user may want to learn the structure of a peptide with a desired membrane permeability or biopersistence. In this respect, information on which portion of the structure of a peptide to change to form a peptide with a more preferable membrane permeability or biopersistence is useful information for the user designing the peptide.

Accordingly, the information processing system according to the second exemplary embodiment identifies a residue among plural residues structuring a peptide that particularly affects the prediction information, and presents this residue to the user as a substitution candidate residue. Thus, a search for a peptide with a more preferable membrane permeability or biopersistence may be assisted, and a navigation service relating to design of the peptide may be provided to the user.

Figure 10:
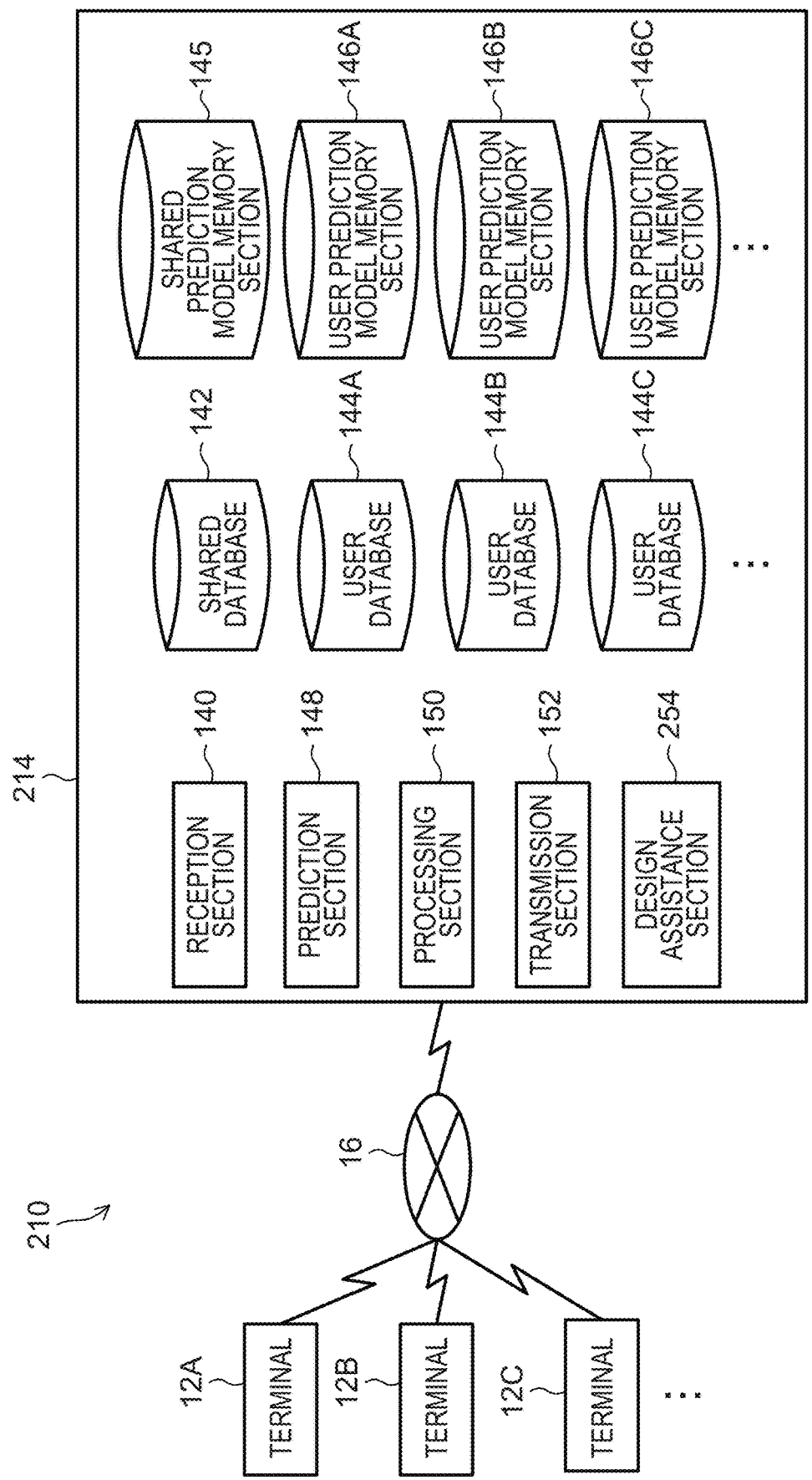
FIG. 10 is a block diagram showing an information processing system according to a second exemplary embodiment.

FIG. 10 is a block diagram showing an example of structures of an information processing system 210 according to the second exemplary embodiment. As shown in FIG. 10, a server 214 of the information processing system 210 according to the second exemplary embodiment is additionally provided with a design assistance section 254. The design assistance section 254 transmits information assisting design of a peptide by a user to the terminal 12. This is described in more specific terms below.

Similarly to the first exemplary embodiment, the prediction section 148 of the server 214 of the information processing system 210 according to the second exemplary embodiment generates prediction information of a peptide with a trained model such as a neural network or the like. Also similarly to the first exemplary embodiment, the prediction section 148 of the information processing system 210 generates prediction information by extracting a feature vector x to serve as feature information from peptide information of the peptide that is an object of prediction and inputting the feature vector x into the trained model.

The feature vector x is obtained from each of plural residues of the peptide. For example, in a vector x that is $[x_{11}, x_{12}, \ldots x_{21}, x_{22}, \ldots x_{N1}, x_{N2}, \ldots ]$, $[x_{11}, x_{12}, \ldots ]$ is a vector obtained from a first residue included in the peptide, $[x_{21}, x_{22}, \ldots ]$ is a vector obtained from a second residue included in the peptide, and $[x_{N1}, x_{N2}, \ldots ]$ is a vector obtained from an N-th residue included in the peptide.

First, for each of the plural residues structuring the peptide, the design assistance section 254 uses, for example, previously known technology to analyze parameters of the trained model that generate prediction information of peptides. Thus, the design assistance section 254 computes scores (below referred to simply as "residue effect scores") representing degrees to which the residues affect the prediction information.

More specifically, the design assistance section 254 first calculates a differential value for each element $x_{ij}$ of the feature vector x inputted into the trained model, by partial differentiation of a value y that represents the prediction information outputted from the trained model with respect to the element $x_{ij}$. The partial differentiation of the value y with respect to the element $x_{ij}$ is represented by the following expression.

$$\frac{\partial y}{\partial x_{ij}}$$

These differential values are obtained by analyzing parameters of the trained model. Absolute values of the following differential values are used as scores (below referred to simply as "feature quantity effect scores") representing degrees to which the feature values of an i-th residue affect the prediction information.

$$\frac{\partial y}{\partial x_{i1}}, \frac{\partial y}{\partial x_{i2}}, \cdots,$$

The design assistance section 254 calculates a feature quantity effect score for each element $x_{ij}$ of the feature vector x.

Figure 11:
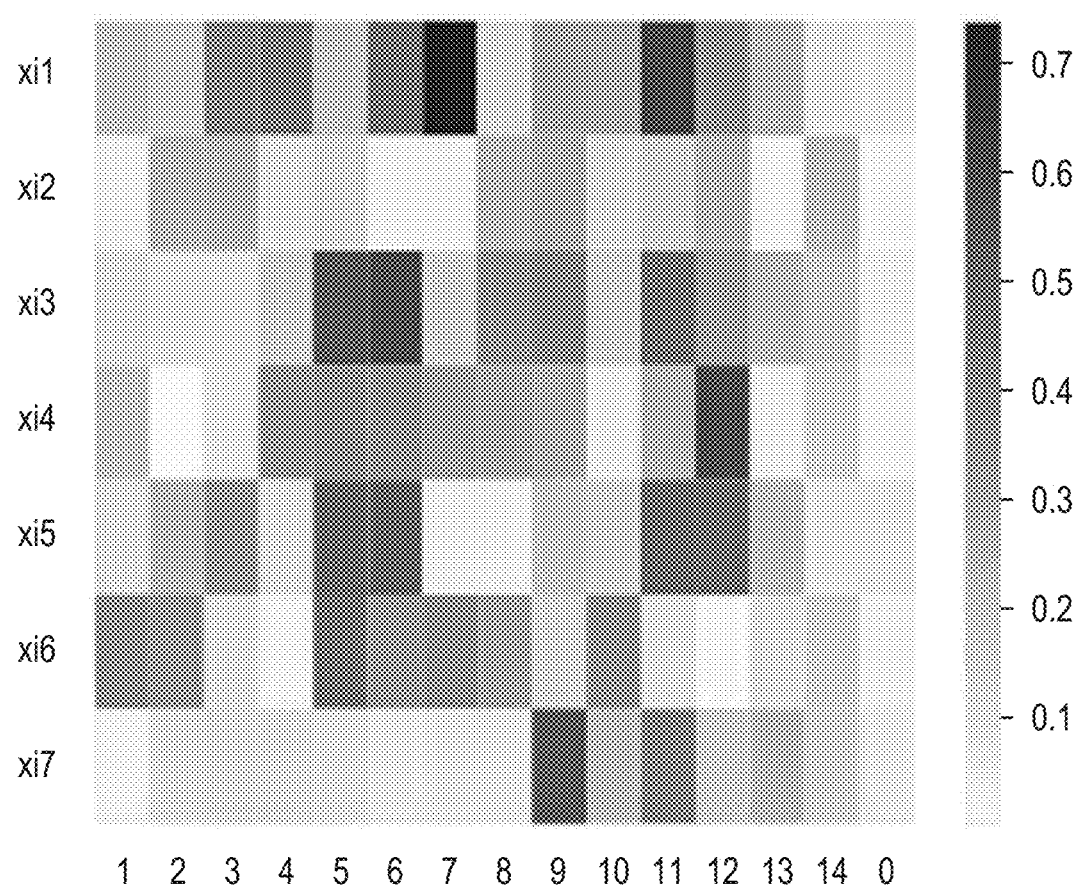
FIG. 11 is a diagram describing scores according to the second exemplary embodiment.

FIG. 11 is a diagram describing the feature quantity effect scores according to the present exemplary embodiment. FIG. 11 is what is referred to in other fields as a saliency map.

In the map shown in FIG. 11, the symbols 1, 2, etc. along the horizontal axis represent identifiers of residues, and the symbols along the vertical axis represent types of feature quantities contained in a feature vector x. Dark and light parts of the map correspond to the feature quantity effect scores representing degrees to which the elements of the feature vector x affect predictions, with darker parts of the map representing higher feature quantity effect scores.

In the example in FIG. 11, for example, the feature quantity effect score of element $x_{71}$ of the feature vector of the residue whose identifier is 7 is high. Therefore, it can be expected that substituting the residue whose identifier is 7 with a different residue or the like will greatly alter the prediction information. The direction of the effect of the presence of this residue may be revealed by checking whether the differential values corresponding to the feature quantity effect scores are positive or negative.

Then, for each of the plural residues, for example, by calculating a sum of the feature quantity effect scores calculated for the corresponding elements of the feature vector x or the like, the design assistance section 254 calculates the residue effect score of that residue. The design assistance section 254 then identifies, from the residue effect scores of the residues that are calculated for each of the plural residues, residues with a residue effect score that is at least a predetermined threshold value.

A method for calculating a residue effect score from feature quantity effect scores is not limited to the technique described above. For example, a weighted average, maximum, minimum or the like of the feature quantity effect scores calculated for the corresponding elements of the feature vector x may be used as a residue effect score.

Then, the design assistance section 254 specifies the identified residues in the structure of the peptide as substitution candidate residues and sets the substitution candidate residues as modification site candidates.

For example, the design assistance section 254 specifies residues with residue effect scores of at least the predetermined threshold value as being modification site candidates, and the design assistance section 254 generates design assistance information suggesting the substitution candidate residues.

The transmission section 152 of the server 214 according to the second exemplary embodiment transmits the design assistance information generated by the design assistance section 254 to the terminal 12. The transmission section 152 may transmit a map such as that illustrated in FIG. 11 to the terminal 12 as the design assistance information.

Other structures and operations of the information processing system 210 according to the second exemplary embodiment are the same as in the first exemplary embodiment, so are not described here.

As described above, for each of plural residues structuring a peptide, the server of the information processing system according to the second exemplary embodiment calculates a residue effect score representing a degree to which the residue affects prediction information, by analyzing parameters of a trained model that generates the prediction information. Among the respective residue effect scores calculated for the plural residues, the server identifies residue effect scores that are at least a predetermined threshold value, specifies the identified residues as substitution candidate residues in the structure of the peptide, and sets the substitution candidate residues as modification site candidates. The server then transmits design assistance information suggesting the modification site candidates to the terminal. The terminal displays the design assistance information transmitted from the server at the display unit (not shown in the drawings). Thus, the user may get hints about which of the residues structuring the peptide could be usefully modified and how, which may assist in design of a peptide by the user.

From the respective residue effect scores calculated for plural residues, the server according to the second exemplary embodiment may identify residues with residue effect scores less than a predetermined threshold value and present information of these residues to the user. In this case, residues whose modification would have very little effect on membrane permeability or biopersistence are identified. Thus, the user may get hints about which of the residues structuring the peptide may be usefully modified.

Third Exemplary Embodiment

Now, a third exemplary embodiment is described. An information processing system according to the third exemplary embodiment differs from the first and second exemplary embodiments in generating plural candidate peptides in each of which at least one residue of the plural residues structuring a peptide is replaced with a pre-specified different residue, generating prediction information for each of the plural candidate peptides, identifying a residue that affects the prediction information, and specifically suggesting a residue substitution. Structures of the information processing system according to the third exemplary embodiment that are similar to parts of the information processing system according to the second exemplary embodiment are assigned the same reference symbols and are not described here.

The design assistance section 254 of the server 214 according to the third exemplary embodiment generates candidate peptides in each of which at least one residue of plural residues structuring a peptide is replaced with a pre-specified different residue, such as alanine or the like.

Figure 12:
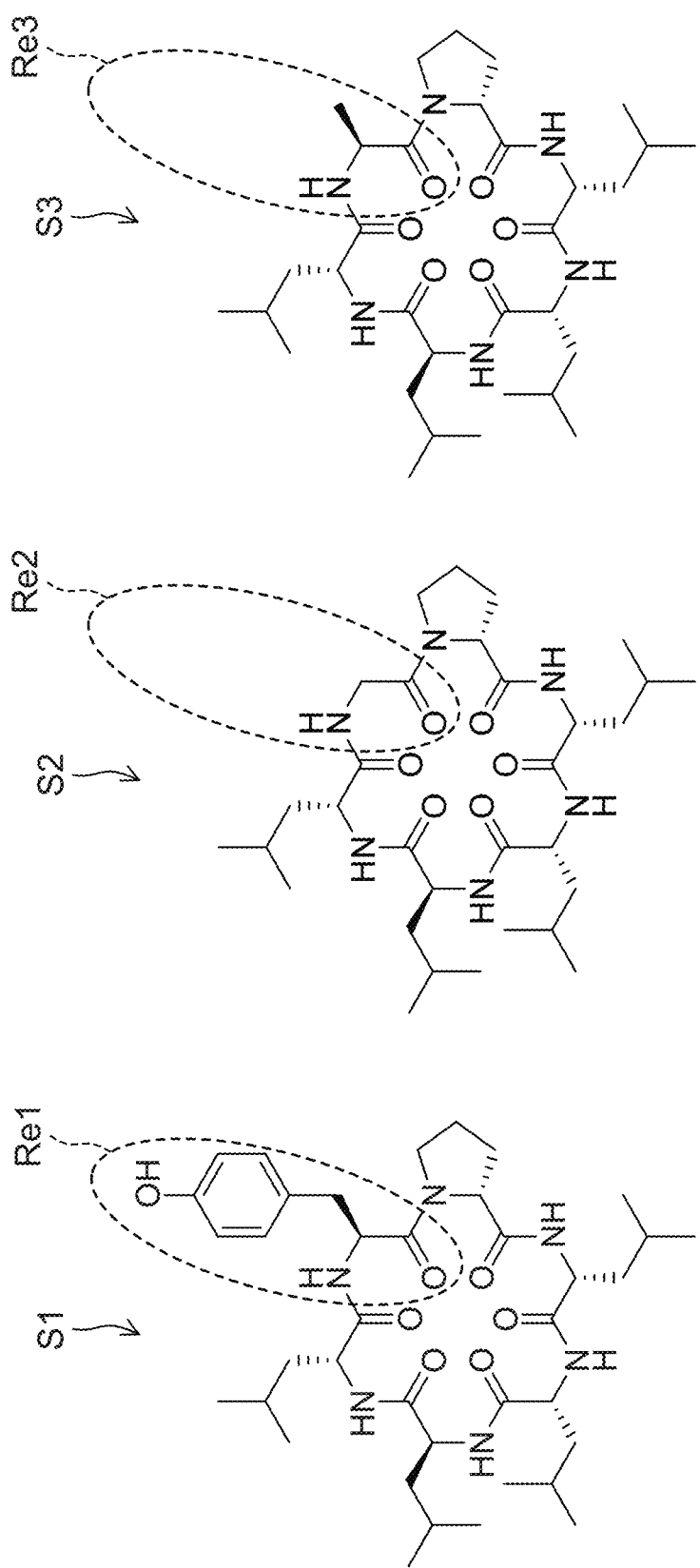
FIG. 12 is diagrams describing candidate peptides.

FIG. 12 is diagrams describing candidate peptides. FIG. 12 shows examples in which a residue Re1 in a peptide S1 is replaced with different residues. For example, the design assistance section 254 generates a candidate peptide S2 by replacing the residue Re1 in the peptide S1 in FIG. 12 with a different residue Re2 (for example, glycine), and the design assistance section 254 generates a candidate peptide S3 by replacing the residue Re1 in the peptide S1 in FIG. 12 with a different residue Re3 (for example, alanine). The different residue may be, for example, a natural amino acid such as valine, leucine, arginine, asparagine or the like, or an arbitrary artificial amino acid or the like.

The prediction section 148 according to the third exemplary embodiment uses a similar technique to the first exemplary embodiment to generate prediction information of a peptide without residue replacement and prediction information for each of plural candidate peptides.

Then, for each of the plural candidate peptides, the design assistance section 254 calculates a difference between the prediction information of the candidate peptide and the prediction information of the peptide without residue replacement. The design assistance section 254 identifies a candidate peptide for which the difference is at least a predetermined threshold value, and identifies the site of the replacement residue in the identified candidate peptide.

When the difference between the prediction information of the peptide without residue replacement and the prediction information of a candidate peptide is large, at least one of the replaced residue and the replacement residue has a large effect on the prediction information. Accordingly, the design assistance section 254 identifies the site of the replacement residue in the candidate peptide for which the difference is large and identifies the residue located at that site in the peptide without residue replacement.

The design assistance section 254 specifies the residue at the identified site in peptide structure information representing the structure of the peptide as a substitution candidate residue, and sets the substitution candidate residue as a modification site candidate. The design assistance section 254 then generates design assistance information suggesting substitution of the substitution candidate residue with the different residue.

FIG. 13 shows examples of design assistance information. As shown in FIG. 13, the design assistance information may include, for example, peptide information before the residue is modified (for example, a structural formula of the peptide), information representing the substitution candidate residue (in the drawing, the dotted line region indicates the substitution candidate residue), and the prediction information of the peptide. As a further example, the design assistance information may include peptide information after the residue is substituted (for example, a structural formula of the peptide), the prediction information of the peptide, and information of the residue that is introduced into the candidate peptide (for example, a structural formula of the residue). A substitution candidate residue may be replaced with plural residues that are different from one another, and the design assistance information may include changes in the prediction information when the substitution candidate residue is replaced thus (or a weighted average of the changes).

The transmission section 152 of the server 214 according to the third exemplary embodiment transmits the design assistance information generated by the design assistance section 254 to the terminal 12.

Other structures and operations of the information processing system 210 according to the third exemplary embodiment are the same as in the first or second exemplary embodiment, so are not described here.

As described above, the server of the information processing system according to the third exemplary embodiment generates plural candidate peptides in each of which at least one of the plural residues structuring a peptide is replaced with a pre-specified different residue, and generates prediction information of the peptide without residue replacement and prediction information of each of the plural candidate peptides. For each of the plural candidate peptides, the server calculates a difference between the prediction information of the peptide without residue replacement and the prediction information of the candidate peptide. The server identifies candidate peptides in which the difference is at least a predetermined threshold value, and identifies sites of the replacement residues in the identified candidate peptides. The server specifies the residues at the identified sites in the peptide structure as substitution candidate residues, and sets the substitution candidate residues as modification site candidates. Thus, a user may get hints about which of the residues structuring the peptide could be usefully modified, which may assist in design of a peptide by the user.

Fourth Exemplary Embodiment

Now, a fourth exemplary embodiment is described. An information processing system according to the fourth exemplary embodiment differs from the first to third exemplary embodiments in awarding points representing compensation to a user when predetermined data is provided from the user. Structures of the information processing system according to the fourth exemplary embodiment that are similar to parts of the information processing system according to the first exemplary embodiment are assigned the same reference symbols and are not described here.

In order to efficiently generate prediction information relating to pharmacokinetics of a peptide, large amounts of data are required. For example, experimental data representing membrane permeabilities or biopersistences obtained by predetermined experiments relating to pharmacokinetics of peptides may be useful data for predicting pharmacokinetics of other peptides.

Accordingly, when predetermined data is provided from a user, the information processing system according to the fourth exemplary embodiment awards points representing compensation to the user. These points can be used for, for example, discounting usage fees of services provided by the information processing system, or the like.

Figure 14:
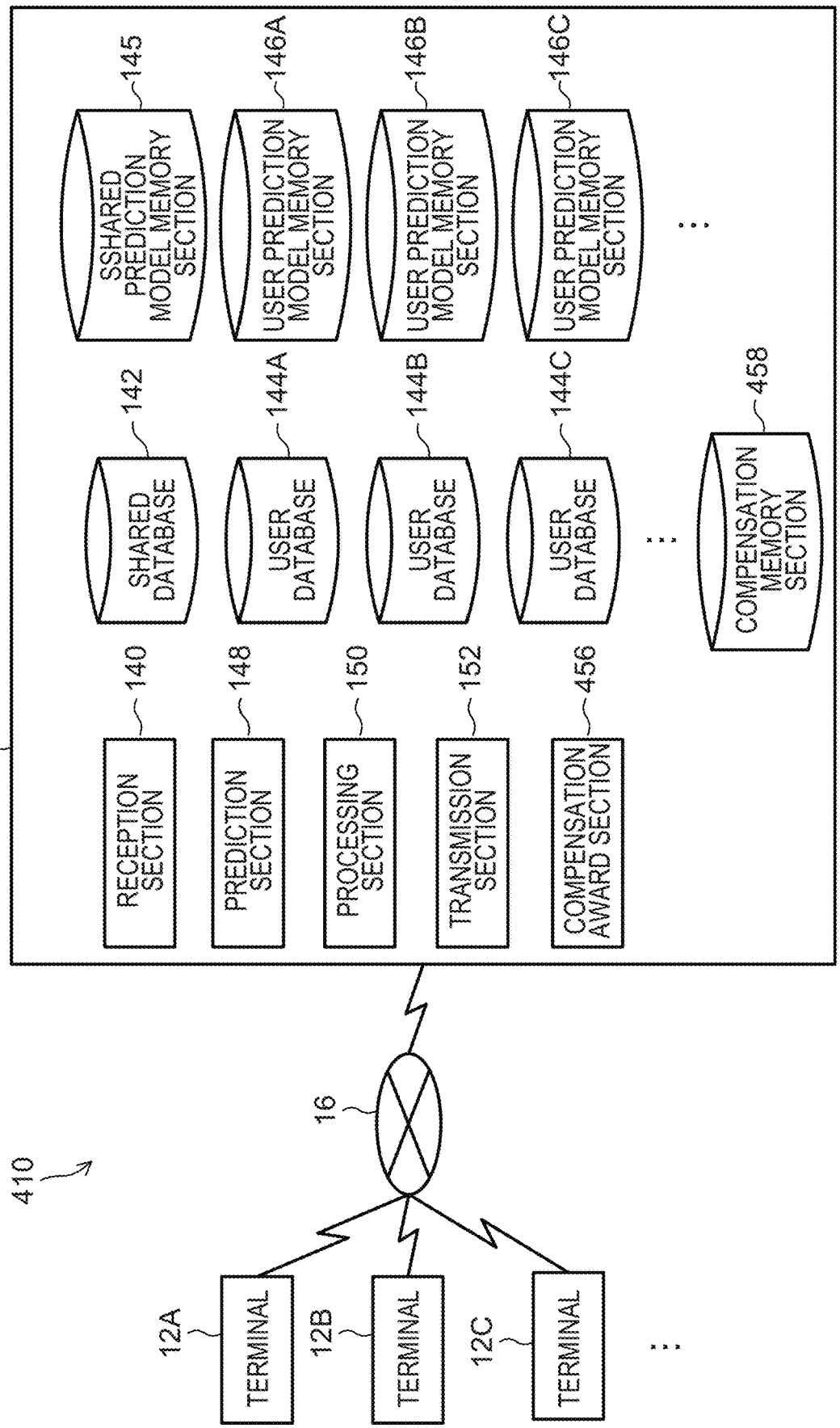
FIG. 14 is a block diagram showing an information processing system according to a fourth exemplary embodiment.

FIG. 14 is a block diagram showing an example of structures of an information processing system 410 according to the fourth exemplary embodiment. As shown in FIG. 14, a server 414 of the information processing system 410 according to the fourth exemplary embodiment is additionally provided with a compensation award section 456 and a compensation memory section 458.

The compensation award section 456 stores data provided from a user into the shared database 142 or the shared prediction model memory section 145. For example, the compensation award section 456 associates at least one kind of data transmitted from the terminal 12 among: experimental data relating to pharmacokinetics of peptides, which is teaching data of prediction information of peptides; information representing an experimental method used to obtain the experimental data; a prediction model saved in the user prediction model memory section 146; a prediction model used by the user at the user's terminal (for example, a prediction model created independently at the user's terminal, a prediction model that the user has brought from elsewhere or the like); and prediction information relating to pharmacokinetics of the peptides that is generated by the user. The compensation award section 456 stores the associated data in the shared database 142 or the shared prediction model memory section 145, which are examples of a memory section administered by the server 414.

The experimental data is data relating to pharmacokinetics of peptides that are objects of prediction, which is obtained by a previously known experimental method. This experimental data is used as, for example, teaching data in the creation of a trained model. The information representing the experimental method used to obtain the experimental data is useful information because the credibility of experimental data varies in accordance with what experimental method is used. When a prediction model that is a trained model created independently by the user or the like is provided, this is similarly useful because a new prediction model may be created on the basis of this prediction model. Prediction information of peptides generated independently by the user is similarly useful.

Accordingly, the compensation award section 456 awards points representing compensation for the provision of this data to the user ID assigned to the terminal 12 transmitting the data.

For example, the compensation award section 456 awards points to the user ID by updating a table stored in the compensation memory section 458 in which user IDs are associated with points assigned to the user IDs.

Figure 15:
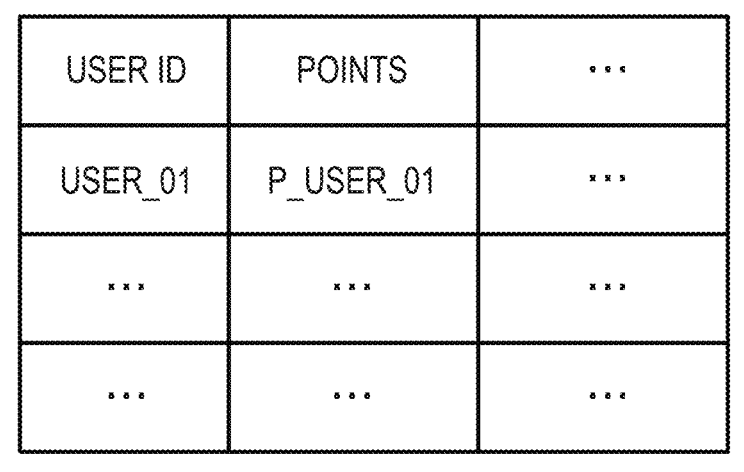

FIG. 15 is an example of the table stored in the compensation memory section 458. In the example shown in FIG. 15, a user ID "USER_01" and points "P_USER_01" awarded to that user ID are shown. When provision of data from the terminal 12 corresponding to the user ID USER_01 is accepted, the compensation award section 456 adds predetermined points to the points P_USER_01 assigned to the user ID USER_01 and updates the table stored in the compensation memory section 458. Rules relating to how many points are awarded for the provision of data are specified beforehand. For example, the compensation award section 456 awards points to a user in accordance with: types of provided data (for example, whether the provided data is data representing experimental values, data representing a prediction model or data representing prediction information); amounts of data; historical information of the data (for example, when the provided data is data representing experimental values of membrane permeability, historical information representing how the data was obtained, from PAMPA testing, Caco-2 cells, MDCK cells, LLC-PK1 cells and so forth); categories of data (for example, attributes indicating whether the provided data is data relating to cyclic peptides or data relating to small molecules); and the credibility of the user providing the data. The credibility of a user may be specified manually, and may be specified by a computer such as the server 414. For example, the compensation award section 456 of the server 414 determines the credibility of a user in accordance with a frequency of use of services provided by the information processing system 410, a usage history and the like. For example, the compensation award section 456 specifies a higher credibility for a user with a higher frequency of usage, and the compensation award section 456 specifies a higher reliability for a user with a longer history of use according to the usage history. When the provision of data from a user is accepted, the compensation award section 456 may, for example, calculate an estimate of a level of contribution to performance improvement when the provided data is incorporated in a prediction model, and may alter the points awarded to the user in accordance with this estimate. For example, the compensation award section 456 calculates a level of similarity between the data provided from the user and data that the server 414 already has, and awards higher points to a user providing data with a low level of similarity. Thus, provision of data that the server 414 does not already have is encouraged. As a further example, when data that is expected to adversely affect peptide prediction is provided, the compensation award section 456 may decide not to award points.

Thus, because incentives to provide data are given to users, large amounts of data may be stored in the shared database 142 or shared prediction model memory section 145 of the server 414, and this data may be useful for predicting pharmacokinetics of peptides. The awarding of points in response to the provision of a prediction model is substantially similar to the above descriptions. For example, experimental data provided beforehand that is judged to be correct may be used to estimate the performance of a provided prediction model, and higher points may be awarded for a prediction model that can be expected to provide excellent performance. As a further example, high points may be awarded for a prediction model that improves predictions for peptides for which a previous prediction model has given poor results.

As described above, the server of the information processing system according to the fourth exemplary embodiment awards points representing compensation for the provision of data to a user ID associated with a terminal when one or more of these kinds of data is transmitted from the terminal and stored in a memory section administered by the server: experimental data to be teaching data for prediction information of peptides; information representing an experimental method used when the experimental data was obtained; a prediction model used by the user; and prediction information relating to pharmacokinetics of peptides that is generated by the user. Thus, greater amounts of data that is useful for predictions of pharmacokinetics of peptides may be collected.

The present disclosure is not limited by the exemplary embodiments described above; various modifications and applications are possible within a scope not departing from the gist of the disclosure.

In the above descriptions, modes are described in which a program relating to the present disclosure is memorized in advance (installed) in a memory section (not shown in the drawings), but the program according to the present disclosure may be provided in a mode recorded on a recording medium such as a CD-ROM, a DVD-ROM, a microSD card or the like.

The processing that, in the exemplary embodiments described above, is executed by CPUs reading software (programs) may be executed by various kinds of processor other than a CPU. Examples of processors in these cases include a PLD (programmable logic device) in which a circuit configuration can be modified after manufacturing, such as an FPGA (field programmable gate array) or the like, a dedicated electronic circuit which is a processor with a circuit configuration that is specially designed to execute specific processing, such as an ASIC (application-specific integrated circuit) or the like, and so forth. The processing may be executed by one of these various kinds of processors, and may be executed by a combination of two or more processors of the same or different kinds (for example, plural FPGAs, a combination of a CPU with an FPGA, or the like). Hardware structures of these various kinds of processors are, to be more specific, electronic circuits combining circuit components such as semiconductor components and the like.

The processing according to the present exemplary embodiments may be configured by a computer, server or the like provided with an arithmetic processing unit and a memory unit or the like, and the processing may be executed by a program. The program may be memorized in the memory unit, may be recorded on a recording medium such as a magnetic disc, an optical disc, a semiconductor memory or the like, and may be provided via a network. It will be clear that other structural elements need not necessarily be realized by a single computer or server but may be distributed between plural computers connected by a network.

The disclosures of Japanese Patent Application No. 2020-189856, filed on Nov. 13, 2020, and Japanese Patent Application No. 2021-023750, filed on Feb. 17, 2021, are incorporated herein by reference in their entirety. All publications, patent applications, and technical standards mentioned in this specification are herein incorporated by reference to the same extent as if each individual publication, patent application, or technical standard was specifically and individually indicated to be incorporated by reference.

What is claimed is:

1. An information processing device to receive confidential user peptide information, transform the confidential user information into shared feature information, and increase the efficiency estimates of peptide pharmacokinetics comprising:
   a memory, wherein the memory is configured to store securely store confidential peptide information protecting the confidentiality of user peptide information and feature information converted from confidential peptide information;
   wherein the feature information is stored on a shared database, the conversion of the peptide information to feature information is not readily converted into peptide information;
   wherein the peptide feature information is shared by the users without breaching confidentiality;
   wherein the confidential peptide information is stored on a user database accessible only to the user that supplies the confidential information;
   a processor coupled to the memory, the processor being configured to:
   receive request signals transmitted from a terminal over a network connection;
   access and utilize multiple trained machine learning models stored in the memory, wherein the models are trained on at least the shared database datasets of peptide pharmacokinetics data;
   generate prediction information from relating to pharmacokinetics of peptide in response to the request signals, wherein the prediction information includes quantitative estimates of membrane permeability of the peptide or biopersistence of the peptide;
   generate design assistance information including specific modification site candidates among elements structuring the peptide; and wherein the modification site candidates are determined based on the generated prediction information and predefined rules for improving peptide stability and efficacy; and
   transmit the prediction information to the terminal.

2. The information processing device according to claim 1, wherein:
   the request signals include selection information of a prediction model that generates the prediction information,
   the processor being further configured to:
   in accordance with the selection information, select the prediction model from a plurality of prediction models; and
   generate the prediction information of the peptide by: inputting peptide information representing the peptide, wherein the peptide information includes information of one or more of a peptide structural formula, a peptide SMILES code, a peptide primary structure, a peptide secondary structure, a peptide tertiary structure and a peptide quaternary structure, into the selected prediction model.

3. The information processing device according to claim 2, wherein:
   the request signals include a user ID, and
   the plurality of prediction models include prediction models prepared in advance for respective users,
   the processor being further configured to:
   generate the prediction information of the peptide by inputting the peptide information representing the peptide into a prediction model among the plurality of prediction models that corresponds with the user ID.

4. The information processing device according to claim 3, wherein the plurality of prediction models include trained models trained in advance with training data prepared in advance for the respective users.

5. The information processing device according to claim 1, wherein:
   the request signals include a user ID,
   the processor being further configured to:
   in accordance with the user ID, store the prediction information in a database corresponding with the user ID among a plurality of databases prepared in advance for respective users.

6. The information processing device according to claim 1, wherein:
   the request signals include a user ID,
   the processor being further configured to:
   in accordance with the user ID, store data transmitted from the terminal in a database corresponding with the user ID among a plurality of databases prepared in advance for respective users.

7. The information processing device according to claim 6, the processor being further configured to:
   restore data relating to pharmacokinetics of a peptide that is transmitted from the terminal in the database.

8. The information processing device according to claim 1, the processor being further configured to:
   transmit the prediction information to the terminal in association with the peptide that is an object of prediction.

9. The information processing device according to claim 1,
   the processor being further configured to:
   analyze parameters of the trained model that generates the prediction information and calculates, for each of a plurality of residues structuring the peptide, a residue effect score representing a degree to which the residue affects the prediction information;
   among the residue effect scores calculated for the plurality of residues, identify a residue with a residue effect score that is at least a predetermined threshold value; and
   specify the identified residue as a substitution candidate residue in the structure of the peptide and set the substitution candidate residue as the modification site candidate.

10. The information processing device according to claim 1,
    the processor being further configured to:
    generate a plurality of candidate peptides in each of which at least one residue of a plurality of residues structuring the peptide is replaced with a pre-specified different residue;

generate prediction information of the peptide without residue replacement and prediction information of each of the plurality of candidate peptides;

for each of the plurality of candidate peptides, calculate a difference between the prediction information of the peptide without residue replacement and the prediction information of the candidate peptide, identify a candidate peptide for which the difference is at least a predetermined threshold value, and identify a site of the replaced residue in the identified candidate peptide; and specify the residue at the identified site as a substitution candidate residue in the structure of the peptide and set the substitution candidate residue as the modification site candidate.

11. The information processing device according to claim 1, the processor being further configured to:

when data transmitted from the terminal is stored in the memory administered by the information processing device, award points representing compensation to a user ID assigned to the terminal for provision of the data transmitted from the terminal, the data including at least one of:

experimental data relating to pharmacokinetics of the peptide that is teaching data for prediction information of the peptide, information representing an experimental method when the experimental data was obtained, a prediction model used by the user, or prediction information relating to pharmacokinetics of the peptide that is generated by the user.

12. An information processing method to receive confidential user information, transform the confidential user information into shared feature information, and increase the efficiency of estimates of peptide pharmacokinetics, comprising:

by a processor:

receiving request signals transmitted from a terminal, wherein the processor acts on feature information converted from confidential user peptide information;

generating prediction information relating to pharmacokinetics of a peptide in response to the request signals;

generating design assistance information including a modification site candidate among elements structuring the peptide; and transmitting the generated prediction information to the terminal.

13. A non-transitory recording medium storing an information processing program that is executable by a computer to perform a process to transform the confidential user information into shared feature information and increase the efficiency of estimates of peptide pharmacokinetics, the process comprising:

receiving request signals transmitted from a terminal;

converting confidential user peptide information into peptide feature information;

generating prediction information relating to pharmacokinetics of a peptide in response to the request signals from the recording medium having feature information converted from confidential user peptide information;

generating design assistance information including a modification site candidate among elements structuring the peptide; and transmitting the generated prediction information to the terminal.

14. The information processing system to receive confidential user information, transform the confidential user information into shared feature information, and increase the efficiency of estimates of pharmacokinetics of peptides, comprising a terminal and an information processing device, wherein:

the terminal transmits request signals to the information processing device;

the information processing device receives the request signals transmitted from the terminal, peptide feature information converted from confidential user peptide information and generates prediction information relating to pharmacokinetics of a peptide in response to the request signals, and transmits the generated prediction information to the terminal;

the information processing device generates design assistance information including a modification site candidate among elements structuring the peptide, and transmits the design assistance information to the terminal; and the terminal displays both the prediction information transmitted from the information processing device and the design assistance information at the display unit.

* * * * *